United States Patent [19]

Goerg et al.

[11] Patent Number: 5,776,123
[45] Date of Patent: Jul. 7, 1998

[54] GARMENT WITH TACTILE POSITION INDICATORS

[75] Inventors: Charles Herbert Goerg, Appleton; Gregory James Hess, Fremont, both of Wis.

[73] Assignee: Kimberly-Clark Worldwide, Inc., Neenah, Wis.

[21] Appl. No.: 98,558

[22] Filed: Jul. 28, 1993

[51] Int. Cl.$^6$ .................................................. A61F 13/15
[52] U.S. Cl. .................. 604/391; 601/385.1; 601/385.2; 601/386; 601/389; 116/205; 116/DIG. 17
[58] Field of Search .................. 604/379, 380, 604/384–402; 128/DIG. 18; 116/205, DIG. 17; 24/306; 434/112–115

[56] References Cited

U.S. PATENT DOCUMENTS

| | | | |
|---|---|---|---|
| 2,536,631 | 1/1951 | Ely | 116/205 |
| 3,081,772 | 3/1963 | Brooks et al. | 128/287 |
| 3,635,221 | 1/1972 | Champaign, Jr. | 604/401 |
| 3,638,651 | 2/1972 | Torr | 128/284 |
| 3,646,937 | 3/1972 | Gellert | 128/287 |
| 3,856,008 | 12/1974 | Fowler et al. | 128/165 |
| 3,867,940 | 2/1975 | Mesek et al. | 604/390 |
| 3,869,761 | 3/1975 | Schaar | 24/73 VA |
| 4,036,233 | 7/1977 | Kozak | 128/287 |
| 4,051,853 | 10/1977 | Egan, Jr. | 604/390 |
| 4,063,559 | 12/1977 | Tritsch | 604/360 |
| 4,237,889 | 12/1980 | Gobran | 604/389 |
| 4,315,508 | 2/1982 | Bolick | 128/289 |
| 4,340,563 | 7/1982 | Appel et al. | 264/518 |
| 4,388,075 | 6/1983 | Mesek et al. | 604/385 |
| 4,404,764 | 9/1983 | Wills et al. | 434/113 |
| 4,405,297 | 9/1983 | Appel et al. | 425/72 S |
| 4,500,316 | 2/1985 | Damico | 604/385.1 |
| 4,650,421 | 3/1987 | Anczorwski | 434/113 |
| 4,753,649 | 6/1988 | Pazdernik | 604/389 |
| 4,798,603 | 1/1989 | Meyer et al. | 604/378 |
| 4,808,177 | 2/1989 | DesMarais et al | 604/388.2 |
| 4,909,802 | 3/1990 | Ahr et al. | 604/385.1 |
| 4,936,840 | 6/1990 | Proxmire | 604/385.2 |
| 4,938,754 | 7/1990 | Mesek | 604/385.2 |
| 5,061,262 | 10/1991 | Chen et al. | 604/389 |
| 5,151,092 | 9/1992 | Buell et al. | 604/385.1 |
| 5,275,588 | 1/1994 | Matsumoto et al. | 604/372 |
| B1 4,662,875 | 4/1989 | Hirotsu et al. | 604/389 |

FOREIGN PATENT DOCUMENTS

| | | | |
|---|---|---|---|
| 0080647A1 | 11/1982 | European Pat. Off. | |
| 0532805 | 3/1993 | European Pat. Off. | 604/389 |
| 2122164 | 8/1972 | France | |
| 1263391 | 3/1968 | Germany | |
| 1809372 | 6/1970 | Germany | 604/401 |
| 1095397 | 12/1967 | United Kingdom | |
| 2135568 | 9/1984 | United Kingdom | |

*Primary Examiner*—John G. Weiss
*Assistant Examiner*—K. M. Reichle
*Attorney, Agent, or Firm*—Patricia A. Charlier; Thomas M. Gage

[57] ABSTRACT

A garment includes a garment shell defining a first waist section, an opposite second waist section, and a crotch section therebetween. At least one loop fastening element is attached to the first waist section. A plurality of tactile position indicators are operatively associated with the loop fastening element. The wearer can properly align and secure the garment on himself or herself by identifying the location of the tactile position indicators and releasably connecting portions of the second waist section to the loop fastening element. The invention is particularly useful with disposable absorbent articles worn by adults, and may alternately be employed with tape members.

18 Claims, 7 Drawing Sheets

GARMENT WITH TACTILE POSITION INDICATORS

BACKGROUND OF THE INVENTION

The present invention relates generally to the field of garments with attachment systems. More particularly, the invention pertains to an absorbent article with an improved attachment system that allows the wearer to properly position the absorbent article.

The present invention is intended for use with a wide variety of garments that are to be worn in the crotch region. Such garments may include disposable absorbent articles, underwear, bathing suits, athletic supporters, prosthetics, or other personal care or health care garments. With particular reference to disposable absorbent articles, these articles include such things as incontinence garments, briefs, training pants, diapers, or the like.

Disposable absorbent articles are typically positioned on the wearer and then secured in place with the attachment system. When positioning the absorbent article, one must consider the front-to-back and side-to-side alignments of the absorbent article, as well as the tightness of the attachment system. During use, the attachment system may be released to permit inspection of the absorbent article and then reattached. Alternately, the attachment system may be released and the absorbent article removed, and then a replacement absorbent article can be positioned about and secured to the wearer.

To facilitate the positioning of disposable absorbent articles on the wearer, such garments have heretofore been provided with visual indicators of attachment points on the garment. Visual indicators enable an individual who is fitting an absorbent article to a wearer to identify a particularly desirable attachment position for both the current and replacement absorbent articles. Such visual indicators are particularly suited to garments such as diapers, where a person other than the wearer is positioning and securing the product in place.

Unfortunately, however, visual indicators are inconvenient and often inadequate to assist a wearer when positioning a product such as an incontinence product on himself or herself. The incontinent adult may be unable to position himself or herself to see the absorbent article from multiple angles, particularly in the abdomen and buttocks areas.

SUMMARY OF THE INVENTION

In response to the discussed shortcomings of previous garment attachment systems, a new garment has been discovered. A garment according to the present invention includes a garment shell that defines a first waist section, an opposite second waist section, and a crotch section between the first and second waist sections. At least one first fastening element is attached to or formed from the garment shell in the first waist section, and a plurality of tactile position indicators are operatively associated with the first fastening element. Additionally, portions of the second waist section are releasably connected to the first fastening element by at least one second fastening element that is releasably engageable with the first fastening element. This aspect of the invention allows the wearer to identify the proper attachment position by touch rather than sight. The wearer need not contort uncomfortably in order to observe visual attachment indicators. Rather, the wearer can simply select the discrete attachment points, as defined by the tactile position indicators, which provide the best alignment and securement of the garment.

The tactile position indicators are sized and shaped to be perceptible by touch and are positioned so as to be associated with the first fastening element. While the size of the tactile position indicators may depend on the intended wearer of the garment, the indicators desirably form a perceptible surface irregularity having a dimension of at least about 1 millimeter, particularly from about 1 to about 10 millimeters. The tactile position indicators are preferably associated with a loop fastening element of a hook-and-loop fastening system. Alternately, the hook-and-loop fastening elements may be reversed such that the tactile position indicators are associated with a hook fastening element.

The tactile position indicators may be formed in a wide variety of ways. For example, the first fastening element could be formed with one or more contoured sides to define the tactile position indicators. Alternately, a thermally setting material could be attached to or adjacent the first fastening element to define the tactile position indicators. Still alternately, the first fastening element could include ridges that are identifiable by touch to define the tactile position indicators. These ridges could be formed by fold lines in the first fastening element, strand segments positioned beneath the first fastening elements, or other suitable means.

The present invention is particularly suitable for disposable absorbent articles. In one embodiment, a disposable absorbent article of the invention includes a garment shell having opposite first and second ends with sides extending between the ends. The garment shell defines a first waist section adjacent the first end, a second waist section adjacent the second end, and a crotch section between the first and second waist sections. The garment shell includes a substantially liquid-permeable liner, a substantially liquid-impermeable backing sheet attached to the liner, and an absorbent core sandwiched therebetween. The disposable absorbent article also includes two loop fastening elements attached to the first waist section, with one loop fastening element associated with each side of the garment shell. A plurality of discrete tactile position indicators are operatively associated with each loop fastening element. Two hook fastening elements are connected to the second waist section and are releasably engageable with the loop fastening elements. This aspect of the invention allows the wearer to feel the proper location for attachment of hook-and-loop fasteners.

The present invention may be incorporated into the commonly recognized adult incontinence product forms. For example, a disposable absorbent article of the undergarment type further includes a pair of strap members with a hook fastening element attached to a first end of each strap member. The absorbent article also includes two additional loop fastening elements and two additional hook fastening elements. One of the additional hook fastening elements is attached to a second end of each strap member. Both additional loop fastening elements are attached to the second waist section, and a plurality of discrete tactile position indicators are operatively associated with each additional loop fastening element. Alternately, a disposable absorbent article of the brief type may further include four additional loop fastening elements attached to the first waist section and four additional hook fastening elements attached to the second waist section. A plurality of discrete tactile position indicators are operatively associated with each additional loop fastening element.

The present invention may also utilize fasteners other than hook-and-loop type fasteners. By way of illustration, an alternate embodiment of an absorbent article according to the invention includes a garment shell with at least one first fastening element attached to or formed from the garment shell in the first waist section. The first fastening element has a plurality of discrete tactile position indicators operatively associated with it. At least two tape members are attached to the second waist section of the garment shell and are releasably engageable with the first fastening element. This aspect allows the wearer to feel a precise location for attachment of a tape fastener. The first fastening element may comprise either a portion of the garment shell adapted to engage the tape members or a separate tape landing pad attached to the garment shell.

In the preferred embodiments, the backing sheet has a continuous perimeter and is uninterrupted within the perimeter. Thus, there are no holes, slits, apertures, or the like within the continuous boundary of the backing sheet. This aspect is particularly significant in the context of disposable absorbent articles, where slits, holes, apertures, or the like can detract from product performance.

Another aspect of the invention pertains to a method of making a disposable absorbent article. The method includes providing a garment shell and releasably engageable first and second fastening elements. The method also includes forming a plurality of tactile position indicators and attaching the first fastening elements to the garment shell so that a plurality of discrete tactile position indicators are operatively associated with each first fastening element.

As can be seen from the foregoing, the present invention provides a garment that the wearer can precisely position and secure on himself or herself without having to reposition to visually identify the desired attachment points.

Numerous other objects, features, and advantages of the present invention will appear from the following description. In the description, reference is made to the accompanying drawings which illustrate preferred embodiments of the invention. Such embodiments do not represent the full scope of the invention. Reference should therefore be made to the claims herein for interpreting the full scope of the invention.

DETAILED DESCRIPTION OF THE PREFERRED EMBODIMENTS

Figure 1:
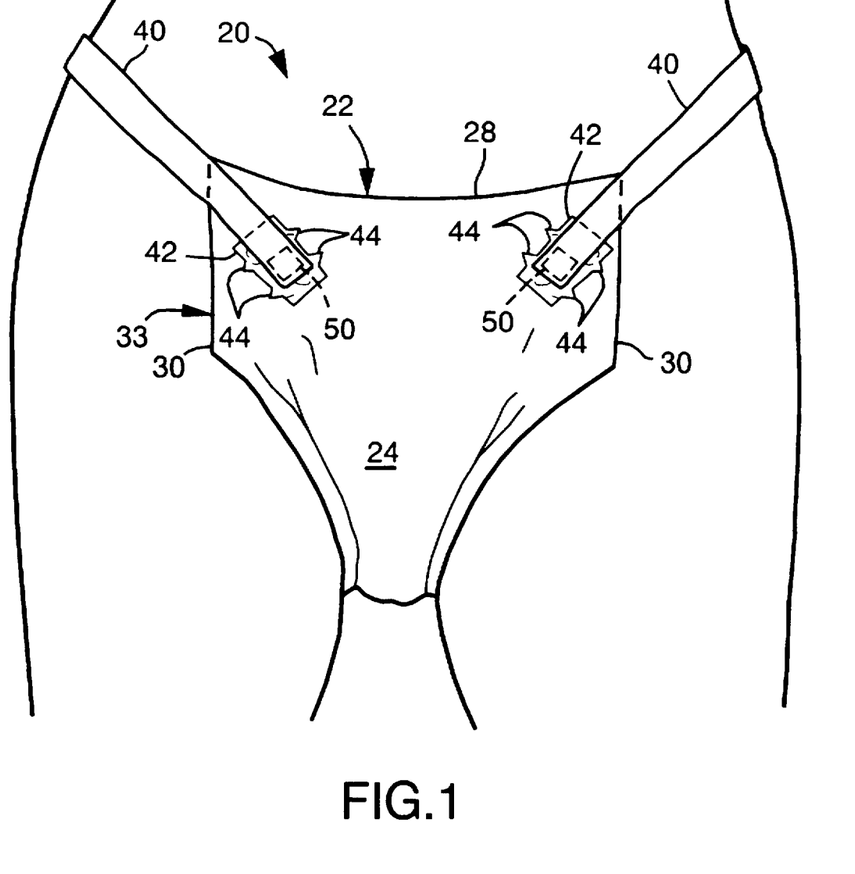
FIG. 1 is a front plan view of a disposable absorbent article according to the present invention, shown during use.
Figure 2:
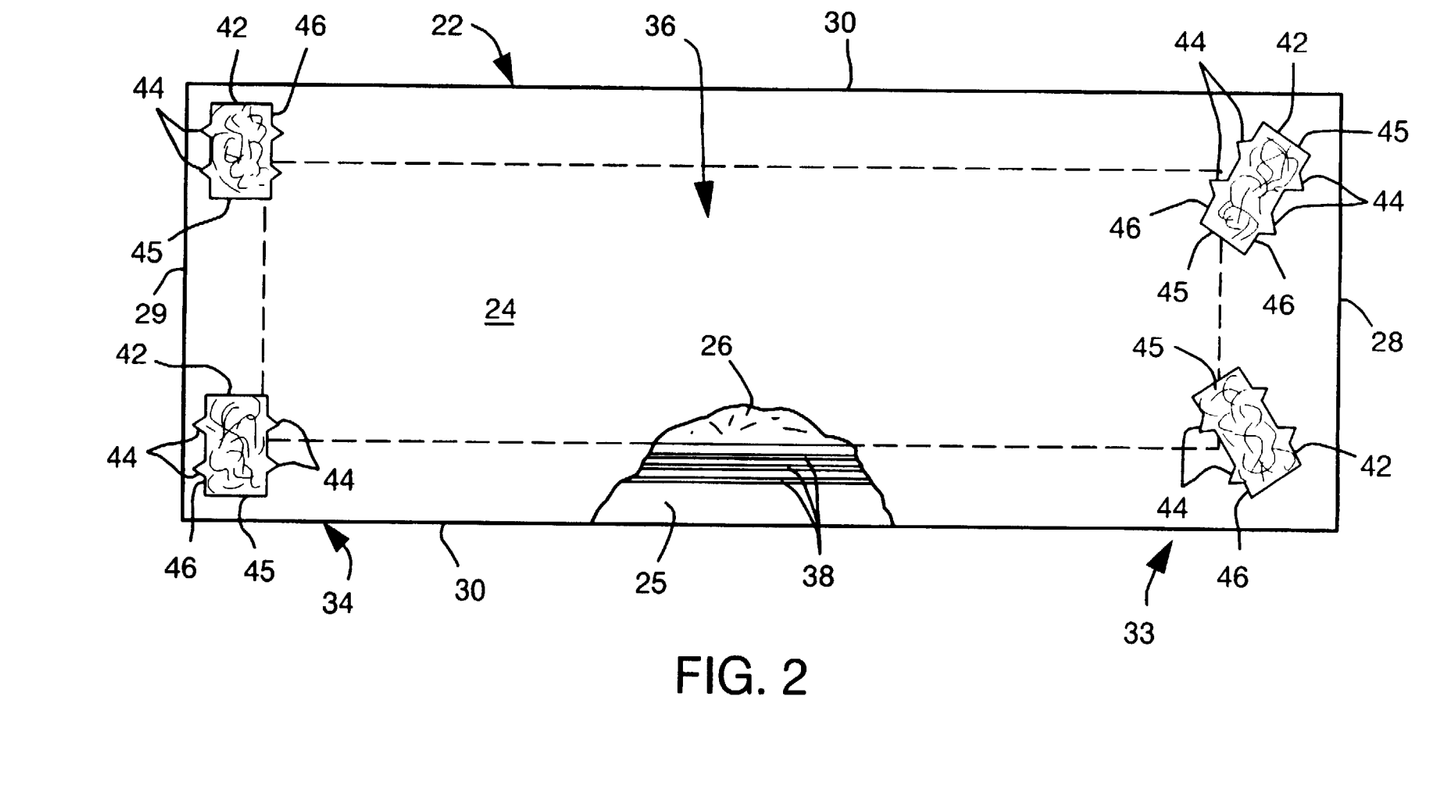
FIG. 2 is a plan view of a garment shell of the disposable absorbent article shown in FIG. 1, with portions broken away for the purposes of illustration.
Figure 3:
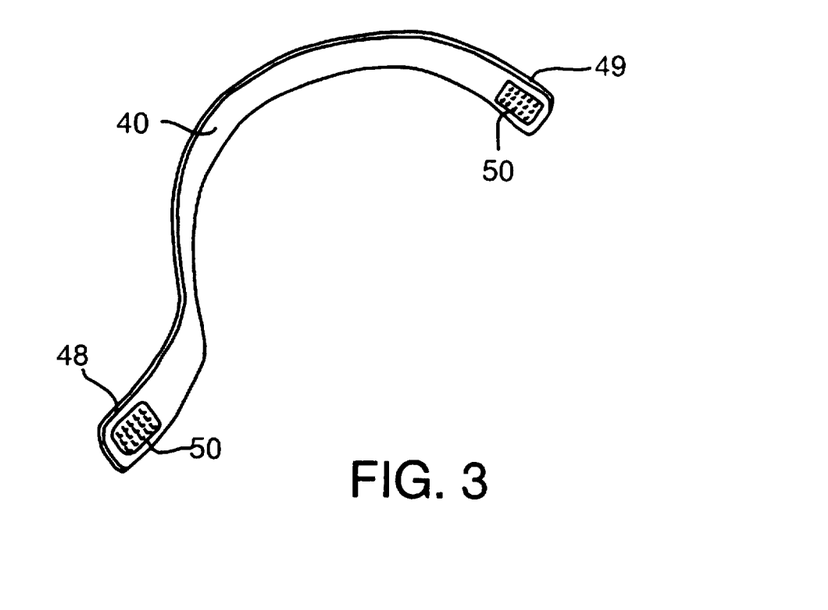
FIG. 3 is a perspective view of a strap member of the disposable absorbent article shown in FIG. 1.

With reference to FIGS. 1-3, a disposable absorbent article 20 formed according to the present invention is shown for purposes of illustration as an incontinence product for adults. The invention may also be embodied in other types of garments, such as other disposable absorbent articles, underwear, bathing suits, athletic supporters, prosthetics, or other personal care or health care garments.

The disposable absorbent article 20 generally includes a garment shell 22 that is adapted to be used in conjunction with an attachment system. As shown, the garment shell 22 includes a substantially liquid impermeable backing sheet 24, a substantially liquid permeable bodyside liner 25, and an absorbent core 26 (FIG. 2) sandwiched between the backing sheet and the bodyside liner. The backing sheet 24 and bodyside liner 25 are preferably longer and wider than the absorbent core 26, so that the peripheries of the backing sheet and bodyside liner form margins which may be sealed together using ultrasonic bonds, thermal bonds, adhesives, or other suitable means. The absorbent core 26 may be attached to the backing sheet 24 and/or the bodyside liner 25 using ultrasonic bonds, adhesives, or other suitable means. The absorbent article 20 may also include additional components to assist in the acquisition, distribution and storage of waste material. For example, the article 20 may include a transport layer, such as described in U.S. Pat. No. 4,798,603 issued Jan. 17, 1989, to Meyer et al., which is incorporated herein by reference.

The garment shell 22 as shown is generally rectangular with a first or front end 28, an opposite second or back end 29, and longitudinal sides 30 extending between the first and second ends. The garment shell 22 defines a first or front waist section 33 adjacent the first end 28 and an opposite second or back waist section 34 adjacent the second end 29. A crotch section 36 is located intermediate the first and second waist sections 33 and 34. When the garment shell 22 is placed on a wearer, the first waist section 33 is generally the portion of the garment located forward of the crotch region of the wearer, and the second waist section is generally the portion of the garment located rearward of the crotch region of the wearer. The garment shell 22 may be rectangular with a length in the range of from about 10 to about 34 inches (ca. 25–86 cm.), and a width in the range of from about 2 to about 22 inches (ca. 5–56 cm.). Of course, the garment shell 22 may optionally be T-shaped, I-shaped, hourglass-shaped, or irregularly-shaped.

The garment shell 22 may include elastic strands or ribbons 38 (FIG. 2) longitudinally orientated along each side margin of the article 20 and attached in a stretched condition to the backing sheet 24, the liner 25, or both. The elastic strands 38 are located in the crotch section 36 and extend toward or into the first and second waist sections 33 and 34. The elastic strands 38 may assist in holding the shell 22 against the body of the wearer or forming seals or gaskets about the leg of the wearer.

The attachment system in the illustrated embodiment includes a pair of strap members 40 and four first fastening elements 42. The first fastening elements 42 are desirably formed of a loop material and accordingly are also termed loop fastening elements. Each loop fastening element 42 is desirably formed with a plurality of discrete tactile position indicators 44 (FIGS. 1 and 2). The tactile position indicators 44 are identifiable or felt by human touch and can be used by the wearer to properly position and secure the absorbent article 20, as explained in greater detail hereinafter.

The loop fastening elements 42 comprise the loop component of a hook-and-loop fastening system, wherein the strap members 40 releasably connect portions of the second waist section 34 and the loop fastening elements located in the first waist section 33. As used herein, the terms "connect" and "connected" refer to the joining, adhering, bonding, attaching, or the like, of two materials or elements. Two materials or elements will be considered to be connected when they are connected directly to one another or indirectly to one another, such as when each is directly connected to intermediate materials or elements.

The four loop fastening elements 42 may be identical in shape and formed of any suitable loop material. The term loop material is intended, in one embodiment, to mean a structure having a base portion and a plurality of loop members extending upwardly from at least one surface of the base portion. The loop material can comprise a fabric material manufactured to have a raised loop construction, stabilized through napping and thermosetting so that the individual loops are erect from the fabric base. The loop material may be formed of any suitable material, such as acrylic, nylon, polypropylene or polyester, and may be formed by methods such as warp knitting, stitch bonding, extruding or needle punching. The loop fastening elements 42 can also be any suitable material having non-woven loops, with or without a base portion.

In a preferred embodiment, the loop fastening elements 42 have a two bar warp knit construction, with from 21 to 41 courses per inch (ca. 8–16 per cm.) and from 26 to 46 wales per inch (ca. 10–18 per cm.), of polyester yarn. In particular, about 15–35 percent of the yarns may be composed of yarn having about 1–30 individual filaments therein and having a yarn denier within the range of about 15–30 d (denier). In addition, about 65–85 percent of the yarns may be composed of yarn having about 1–30 individual filaments therein and having a yarn denier within the range of about 20–55 d. Also, the loops may particularly be formed with a loop height from about 2 to about 2.5 millimeters. The caliper may be from about 0.010 to about 0.040 inch (ca. 0.25–1 mm.) and the basis weight may be from about 1.0 to about 3.0 ounces per square yard (ca. 34–102 grams per square meter). One particular material which has been found suitable for the loop fastening elements 42 is identified as No. 19902 and is available from Guilford Mills of Greensboro, N.C. U.S.A.

Figure 9:
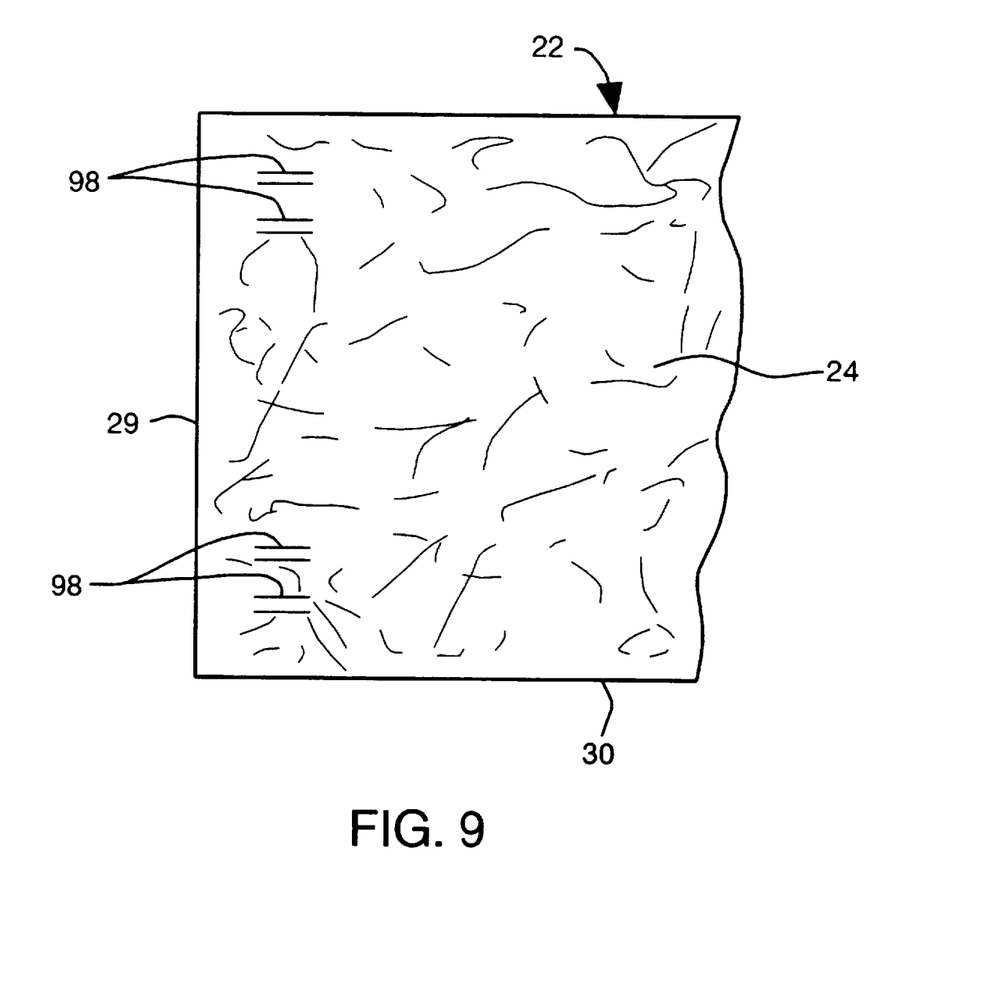
FIG. 9 is a plan view of a portion of an alternate garment shell of a disposable absorbent article of the present invention.

The loop fastening elements 42 are located in the first and second waist sections 33 and 34 and are attached to the surface of the backing sheet 24 that is remote from the bodyside liner 25. The two loop fastening elements 42 in the first waist section 33 are preferably separated from one another and spaced from the first end 28 and the longitudinal sides 30 by at least about 0.25 inch (ca. 6.5 mm.). Correspondingly, the two loop fastening elements 42 in the second waist section 34 are preferably separated from one another and spaced from both the second end 29 and the longitudinal sides 30 by at least about 0.25 inch (ca. 6.5 mm.). Alternately, as discussed hereinafter, the loop fastening elements may be formed from a portion of the backing sheet (FIG. 9).

The loop fastening elements 42 have generally opposite ends 45 and sides 46 extending between the ends (see FIG. 2). In the illustrated embodiment, the contour of the sides 46 defines the shape and position of the tactile position indicators 44. The ends 45 and the sides 46, excluding the tactile position indicators 44, preferably have generally straight edges. The tactile position indicators 44 desirably extend a distance of at least about 1 millimeter from a side edge 46, preferably between about 1 and about 10 millimeters from a side edge, so that they are readily identifiable or felt by human touch. Further, each tactile position indicator 44 may extend along a side edge 46 a distance between about 1 and about 10 millimeters.

Because the tactile position indicators 44 are used to position and secure the absorbent article 20, each individual position indicator must be discrete. Desirably, the tactile position indicators 44 are spaced from one another by at least about 3 millimeters, preferably between about 5 and about 30 millimeters. The minimum spacing is related to the ability of the intended wearer to distinguish different position indicators 44. Both sides 46 preferably although not necessarily have the same number and spacing of tactile position indicators 44. Alternately, only one side 46 of each loop fastening element 42 could be contoured to define the tactile position indicators 44 (not shown). Generally, two or more, particularly two to six, tactile position indicators 44 are present on each side 46.

In the illustrated embodiment, the loop fastening elements 42 are generally rectangular in shape, although other geometric shapes, such as square, oval, irregular, etc., may be suitable. The size of each loop fastening element 42 should be sufficient to provide a range of discrete attachment points as identified by the tactile position indicators 44. For example, each loop fastening element 42 in the first waist section 28 may be generally rectangular and measure about 4 inches by about 1.25 inches (ca. 10 by 3 cm.), and each loop fastening element 42 in the second waist section 29 may be generally rectangular and measure about 1.5 inches by about 2.0 inches (ca. 38 by 51 mm.).

The loop fastening elements 42 are attached by ultrasonic bonds, thermal bonds, stitching, adhesives, or other suitable means, so that the loops of the loop material extend outwardly from the backing sheet 24. As illustrated in FIG. 2, the loop fastening elements 42 in the first waist section 28 are desirably attached such that the long dimension of each fastening element forms an angle of from about 25 to 45 degrees, particularly about 35 degrees, with the transverse axis of the garment shell 22, and the loop fastening elements 42 in the second waist section 29 are desirably attached such that the long dimension of each fastening element is generally parallel to the transverse axis of the garment shell. Alternately, the loop fastening elements may be attached at angles with respect to the longitudinal axis of the garment using a plurality of lines of adhesive (not shown), as disclosed in commonly assigned U.S. patent application Ser. No. 07/998,496 filed Dec. 30, 1992, by D. A. Kuen et al. for a "Garment Attachment System". Still alternately, all loop fastening elements 42 may be aligned with the longitudinal or transverse axes of the garment shell 22 (not shown).

With particular reference to FIG. 3, the strap members 40 are each generally rectangular strips of material having opposite first and second ends 48 and 49. A second fastening element 50 is attached at each end 48 and 49 of each strap member 40. The second fastening elements 50 are desirably formed of a hook material and accordingly are also termed hook fastening elements. The hook fastening elements 50 are releasably engageable with the loop fastening elements 42 and thus form the hook component of the hook-and-loop fastening system. The terms "releasably engaged" and "releasably engageable" as used herein refer to two materials or elements being connected or connectable, wherein the materials or elements tend to remain connected absent a separation force applied to one or both of the materials or elements, and are capable of being separated without substantial permanent deformation. When the absorbent article 20 is worn, the central region between the ends 48 and 49 is positioned against a hip of the wearer.

The strap members 40 are preferably formed of an elastic material, which is capable of stretching to approximately 2.8 to 3 times its relaxed length. The strap members 40 preferably have a relaxed length from about 6 inches to about 16 inches (ca. 15–41 cm.), and a width from about 0.5 inch to about 1.5 inches (ca. 1–4 cm.). For example, each strap member 40 may be 13.5 inches (ca. 34 cm.) long and 1 inch (ca. 2.5 cm.) wide. The ends of the strap members 40 may be bonded by ultrasonics, adhesives or other suitable means to prevent raveling.

The hook fastening elements 50 comprise a single-sided hook material. The hook fastening elements 50 may be of a variety of shapes, such as rectangular and measuring about 0.875 inch by about 1.125 inches (ca. 2.2 by 2.9 cm.). Two hook fastening elements 50 are attached to the same main planar surface of a strap member 40 by ultrasonic bonds, thermal bonds, adhesives, stitches or other suitable means. As illustrated in FIGS. 1 and 3, each hook fastening element 50 is positioned in full face-to-face contact with the strap members 40. Alternately, the hook fastening elements 50 may be positioned such that hook fasteners extend past the ends of the strap members (not shown).

Suitable hook material may be molded or extruded of nylon, polypropylene or another suitable material. Desirable stiffness levels of the hook material may be obtained from polymeric materials having a flexural modulus of about 70,000–120,000 pounds per square inch (ca. $4.83 \times 10^8$–$8.27 \times 10^8$ nt/m$^2$) and a Shore hardness value within the range of about D-40 to D-80, such as D-61. The hook fastening elements 50 desirably contain uni-directional hooks, with the machine direction of the hooks aligned with the longitudinal axis of the strap member 40, and the hooks facing toward the opposite end 48 or 49 of the strap member. One suitable single-sided hook material for the hook fasteners is available from Velcro Industries B.V., Amsterdam, Netherlands or affiliates thereof, and is identified as HTH 708 with No. 22 uni-directional hook pattern. Other suitable hook materials include woven materials with cut monofilaments forming hooks.

The shape, density and polymer composition of the hooks may be selected to obtain desirable peel and shear force resistance values between the hook and loop fastening elements 50 and 42. For instance, a more aggressive hook material may comprise a material with a greater average hook height, a greater percentage of directionally-aligned hooks, or a more aggressive hook shape. As one example, the density of the hook members may be more than 50 hooks per square inch (ca. 8 per square cm.), and more particularly within the range of about 440 to about 1040 hooks per square inch (ca. 68–161 per square cm.), such as about 740 hooks per square inch (ca. 115 per square cm.). The row density may be within the range of about 20 to about 60 rows per linear inch of width (ca. 8–24 per linear cm.), such as about 40 rows per linear inch of width (ca. 16 per linear cm.). The hook members may be hook-shaped, mushroom-shaped, arrow-shaped or any other desired shape.

In use, the wearer generally positions the garment shell 22 on his or her body, for instance, with the first waist section 33 toward the abdomen (see FIG. 1) and the second waist section 34 toward the buttocks. The crotch section 36 is thereby positioned to receive body exudate. Before, during or after such positioning, the wearer attaches the strap members 40 using the tactile position indicators 44 to guide proper positioning. Notably, the wearer will not have to see the fastening elements 42 and 50 or the attachment area in order to select a precise attachment point.

More specifically, the wearer can attach each hook fastening element 50 to a loop fastening element 42 at a tactually identifiable position along the length of the loop material. The wearer can secure the garment 20 evenly on both sides 30 by attaching the hook fastening elements 50 at corresponding positions on each side. The wearer can also adjust the tightness of the strap members 40 in discrete increments as defined by the location of the tactile position indicators 44. For example, if the garment 20 is too tight, the hook fastening elements 50 may be separated from the loop fastening elements 42 and reattached at a position on the loop material that corresponds to a tactile position indicator 44 closer to the nearest side 30. Again, the garment positioning can easily remain balanced by using corresponding positions on each side 30. Additionally, when the wearer switches to a replacement absorbent article 20, the wearer can use previous experience with the tactile position indicators 44 to quickly select the proper attachment points for the replacement absorbent article.

Figure 4:
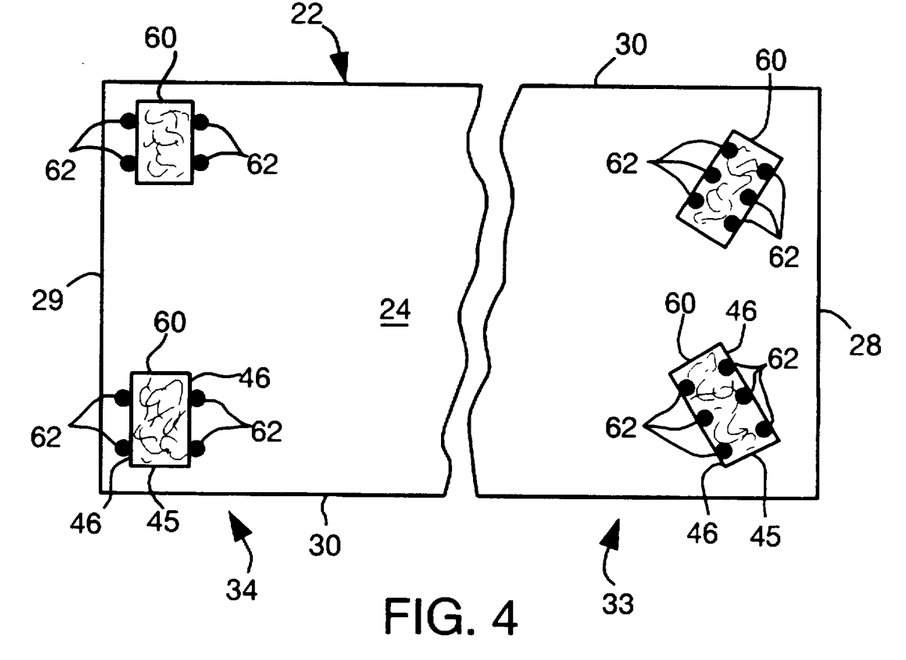
FIG. 4 is a plan view of a garment shell similar to FIG. 2, but showing alternate tactile position indicators of the present invention.
Figure 5:
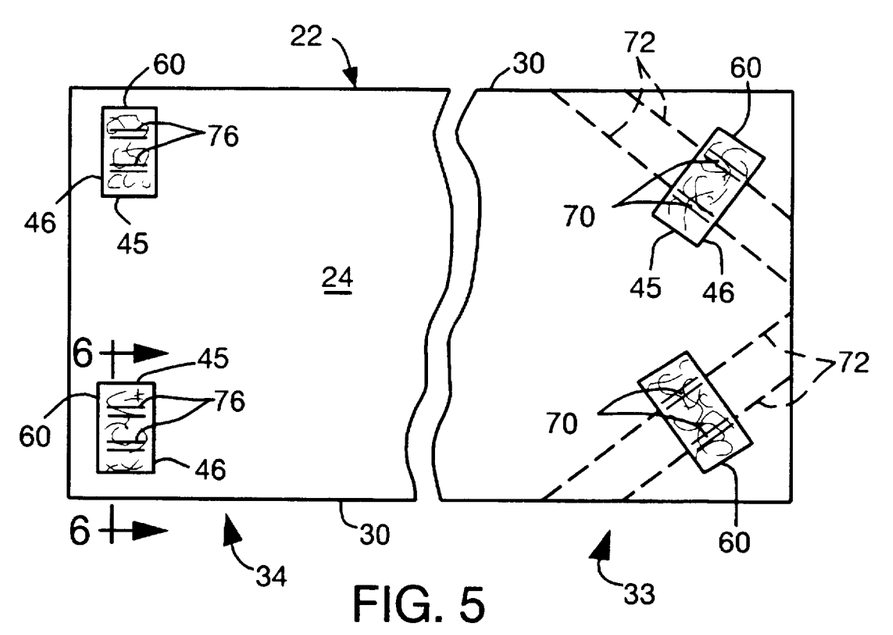
FIG. 5 is a plan view of a garment shell similar to FIGS. 2 and 4, but showing alternate tactile position indicators of the present invention.

Numerous types of tactile position indicators are suitable, including those shown in FIGS. 4 and 5, which illustrate alternate embodiments of the present invention. Components similar to those previously described are labeled with the same reference numeral. With reference to FIG. 4, a garment shell 22 includes a substantially liquid impermeable backing sheet 24, a substantially liquid permeable bodyside liner 25 (not shown), and an absorbent core 26 (not shown) sandwiched therebetween. The garment shell 22 has opposite first and second ends 28 and 29 with sides 30 extending between the ends. The garment shell 22 defines a first waist section 33 adjacent the first end 28, a second waist section 34 adjacent the second end 29, and a crotch section 36 (not shown) therebetween.

The garment shell 22 includes four loop fastening elements 60 of rectangular configuration. The loop fastening elements 60 are attached to the garment shell 22 such that two loop fastening elements are located in each waist section 33 and 34, and one loop fastening element in each waist section is associated with each side of the garment shell.

Each loop fastening element 60 has a plurality of discrete tactile position indicators 62 operatively associated therewith. The term "operatively associated" as used herein refers to the tactile position indicators 62 being spaced sufficiently close to, or formed as part of (FIGS. 1–2), a loop fastening element 60 so that the wearer can identify a portion of the loop fastening element with each discrete position indicator.

With reference to FIG. 4, each loop fastening element 60 includes generally opposite ends 45 and sides 46 extending between the ends. The tactile position indicators 62 in the first waist section 33 are located on the loop fastening element 60 but are positioned toward the sides 46 to minimize any potential interference with the hook and loop attachment. In contrast, the tactile position indicators 62 in the second waist section 34 are positioned adjacent the sides 46 of the loop fastening element 60. Generally, the tactile position indicators 62 are preferably positioned on or formed as part of the loop material, or located within about 20 millimeters of the sides 46, particularly within between about 2 and about 20 millimeters of the sides, so that the wearer can touch both the loop material and the tactile position indicators at the same time.

The tactile position indicators 62 in this embodiment comprise a thermally setting material that is non-tacky at room temperature. The thermally setting material desirably has a melting point less than that of the backing sheet. One suitable material is an ethylene vinyl acetate hot melt adhesive, as disclosed in U.S. Pat. No. 5,061,262 issued Oct. 29, 1991, to Chen et al. which is incorporated herein by reference. Other suitable materials include waxes, resins, polymers, or the like. To be identifiable or felt by human touch in the environment of the absorbent article 20, each tactile position indicator 62 preferably extends at least 0.25 millimeter, more preferably at least about 1 millimeter, from the surface of the backing sheet 24. The tactile position indicators 62 can be circular with a diameter of about 1 millimeter for example, or assume any other shape such as line segments.

The alternate embodiment of the garment shell shown in FIG. 5 is similar to that shown in FIG. 4 with the exception of the tactile position indicators. Each loop fastening element 60 in the first waist section 33 has a plurality of discrete tactile position indicators 70 operatively associated therewith. These tactile position indicators 70 are defined by a plurality of ridges that extend across the loop material. The ridges are created by folding the garment shell 22 along fold lines designated 72 in FIG. 5. The folds create ridges of sufficient distinction to be identifiable or felt by touch.

Figure 6:
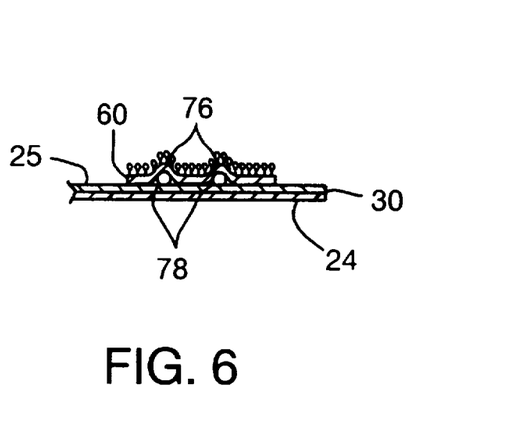
FIG. 6 is an enlarged view in section taken generally from the plane of the line 6—6 in FIG. 5

Each loop fastening element 60 in the second waist section 34 also includes a plurality of discrete tactile position indicators 76 operatively associated therewith. Again, ridges extend across the loop material and define the tactile position indicators 76. In the second waist section 34, however, the ridges are formed by a plurality of parallel strand segments 78 (FIG. 6) positioned between the loop fastening element 60 and the garment shell 22. The strand segments 78 can be any suitable material, such as string, yarn, or tow, a fast-setting adhesive material, natural or man-made polymers or resins, or the like, that will cause the formation of ridges of sufficient distinction to be identifiable or felt by touch. Desirably, the strand segments 78 have a diameter of at least 0.25 millimeter, particularly at least about 1 millimeter.

As suggested by the embodiments of FIGS. 1–7, the tactile position indicators 44, 62, 70, and 76 can by created in many different ways. In order not to detract from performance of the absorbent article 20, however, the backing sheet 24 preferably is free from cuts, slits, punch holes or other openings. Thus, in the illustrated embodiments the backing sheet has a continuous perimeter defined by the ends 28 and 29 and the sides 30 of the garment shell 22, and the backing sheet is uninterrupted by such openings within the perimeter.

Figure 7:
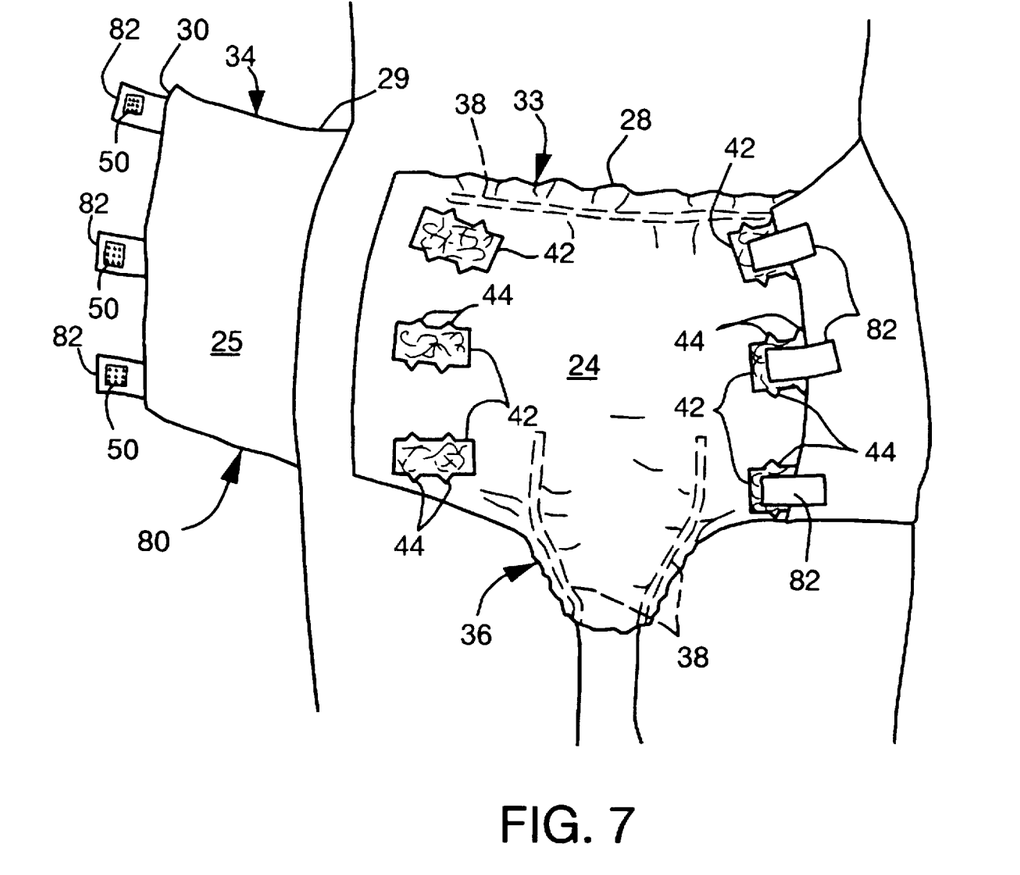
FIG. 7 is a front plan view of an alternate disposable absorbent article of the present invention, shown while the wearer is positioning and securing the absorbent article on himself or herself.

A further alternate embodiment of the invention is illustrated as a brief-type disposable absorbent article 80 of FIG. 7. Like the undergarment-type article 20 shown in FIG. 1, this absorbent article 80 has a garment shell 22 including a backing sheet 24, a bodyside liner 25, and an absorbent core 26 (not shown) sandwiched therebetween. The garment shell 22, which has opposite first and second ends 28 and 29 with sides 30 extending between the ends, defines a first waist section 33 adjacent the first end 28, a second waist section 34 adjacent the second end 29, and a narrow crotch section 36 therebetween. The absorbent article 80 may optionally include elastic strands 38 along each side margin and along each end 28 and 29 stretch bonded to the backing sheet 24, the liner 25, or both.

The attachment system for the absorbent article 80 includes six loop fastening elements 42 attached to the first waist section 33. Three loop fastening elements 42 are generally associated with each side 28 and 29 of the garment shell. Each loop fastening element 42 has a plurality of discrete tactile position indicators 44 operatively associated therewith. The tactile position indicators 44 are similar to those shown in FIGS. 1 and 2 in that they are formed by contoured sides of the loop fastening elements. Alternately, the loop fastening elements could be formed from a portion of the backing sheet (see FIG. 9).

Six fastening tabs 82 are attached to the second waist section 34 of the garment shell 22. The fastening tabs 82 may be formed from, or separately formed and attached to, the backing sheet 24, the liner 25, or both. The fastening tabs 82 are spaced along the sides 30 of the garment shell 22 so that they tend to align with the loop fastening elements 42. A hook fastening element 50, which is releasably engageable with the loop fastening elements 42, is attached to each fastening tab 82.

The wearer can easily determine the specific attachment point of each hook fastening element 50 on each loop fastening element 42 using the tactile position indicators 42. The tactile position indicators allow the wearer to adjust the fit of the absorbent article 80 in discrete increments and balance the position of the garment shell 22 by using corresponding attachment positions on each side 30.

Figure 8:
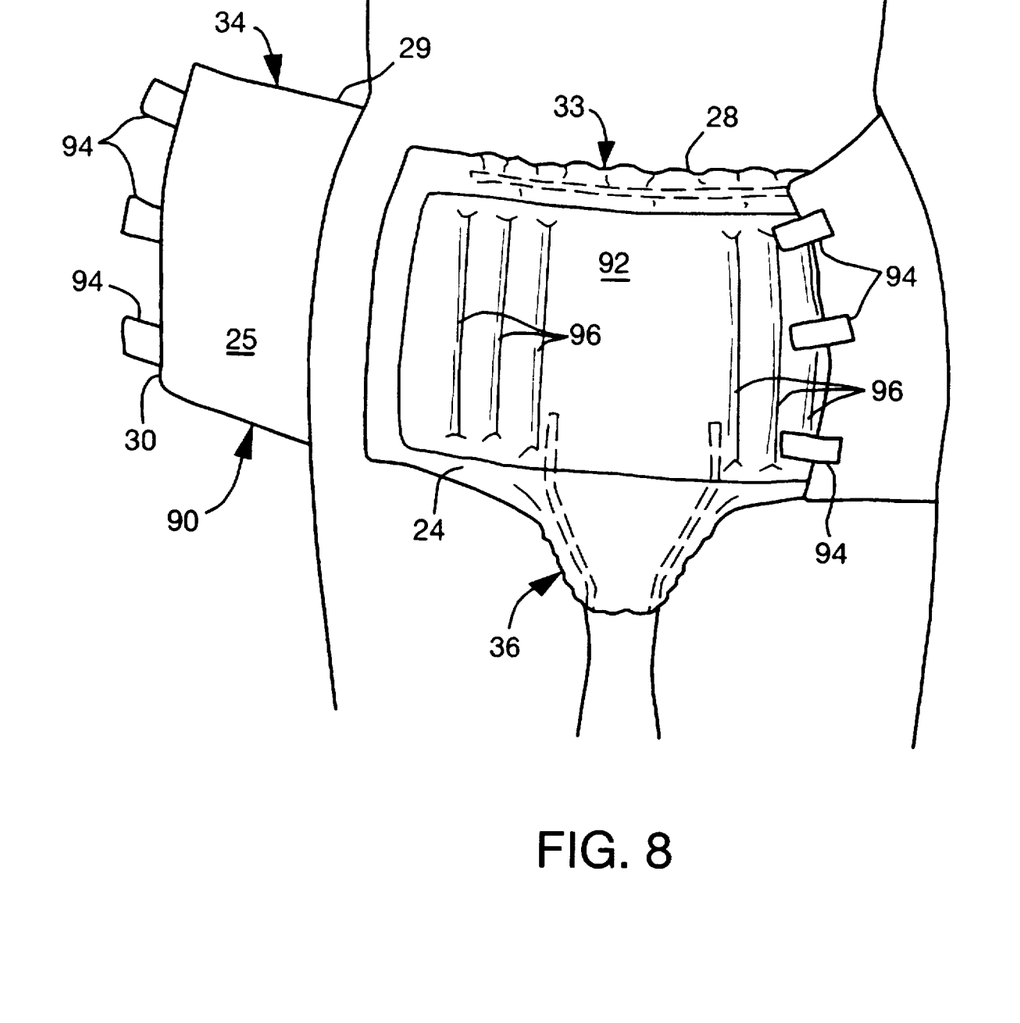
FIG. 8 is a front plan view similar to FIG. 7 of an alternate disposable absorbent article of the present invention.

Another alternate embodiment of the invention is illustrated by absorbent article 90 in FIG. 8. This absorbent article 90 is generally similar to the one shown in FIG. 7 except for the type of first and second fastening elements. A single first fastening element 92 is attached to or formed from the backing sheet 24 in the first waist section 33. Preferably, the first fastening element 92 is in the form of a tape landing pad attached to the backing sheet 24. Six second fastening elements 94 in the form of tape members, preferably although not necessarily refastenable tape members, are directly connected to the second waist section 34. The tape members 94 are thus releasably engageable with the tape landing pad 92 so that the wearer may secure the garment shell 22 about himself or herself.

The tape landing pad 92 and the tape members 94 may be fixed by adhesive or other suitable means to the surface of the backing sheet 24 that is remote from the bodyside liner 25. Each tape member 94 preferably comprises an adhesive surface that is releasably engageable with the tape landing pad 92, and may include a release strip (not shown) to prevent contamination of the adhesive. The tape members 94 and the landing pad 92 may be formed of a polypropylene film and may be constructed in a manner as disclosed in U.S. Pat. No. 4,753,649 issued Jun. 28, 1988, to Pazdernik, which is incorporated herein by reference.

A plurality of discrete tactile position indicators 96 are operatively associated with the tape landing pad 92. The illustrated tactile position indicators 96 are generally parallel to one another and to the sides 30 of the garment shell 22. The position indicators 96 are also spaced from one another so that each represents a different attachment point for a tape member 94. While the length of the tactile position indicators 96 may be such that one set of position indicators is operatively associated with more than one tape member 94 (see FIG. 8), a separate set of position indicators may be provided for each tape member (not shown). Dots, line segments, curves, or other patterns may be used to define the tactile position indicators.

The tactile position indicators 96 may comprise a thermally setting material that is non-tacky at room temperature. Such material may be applied directly to the exposed surface of the tape landing pad 92 during assembly of the absorbent article 90. Alternately, the tactile position indicators 96 may comprise ridges of sufficient distinction to be identifiable or felt by touch. Such ridges may be formed by folding the tape landing pad 92 after it has been attached to the garment shell. Still alternately, the tactile position indicators may be formed by adhesively trapping a plurality of strand segments (not shown) between the tape landing pad 92 and the garment shell 22.

The first fastening element 92 may optionally be formed from all or a portion of the backing sheet 24 in the first waist section 33. Thus, as suggested by FIG. 8, the first fastening element 92 may comprise a portion of the backing sheet adapted to releasably or permanently engage the tape members 94. The tactile position indicators 96 may consequently be formed of a thermally setting material applied to the backing sheet 24, formed of ridges in the backing sheet itself, or formed by strand segments positioned within the backing sheet or between the backing sheet and the liner 25 (not shown).

Use of this absorbent article 90 including the tape fastening system is similar to that described previously in relation to the hook-and-loop fastening system. The wearer can determine a particular attachment point on the first fastening element 92 for each tape member 94 by feeling the position of the tactile position indicators 96. Thus, the wearer is saved from having to visually select an attachment area.

A wide variety of materials may be used to construct the aforementioned components of the article 20, 80 and 90. The backing sheet 24, for example, may comprise a thin, substantially liquid impermeable web or sheet of plastic film such as polyethylene, polypropylene, polyvinyl chloride or similar material. The backing sheet material may be transparent or opaque and have an embossed or matte surface. One preferred material for the backing sheet 24 is a polyethylene film that has a nominal thickness of about 0.001 inch and a systematic matte embossed pattern, and that has been corona treated on both sides. Alternately, the backing sheet 24 may comprise a nonwoven, fibrous web which has been suitably constructed and arranged to be substantially liquid impermeable. Still alternately, the backing sheet may comprise a layered or laminated material, such as a thermally bonded plastic film and nonwoven web composite.

As illustrated in FIG. 9, the backing sheet 24 may also comprise a loop material itself. In this case, several sets of tactile position indicators 98 could be formed in or attached to the loop material, portions of which represent the first fastening elements. The tactile position indicators 98 could be formed by any of the previously-mentioned methods and structures, such as folds, a thermally setting material, strand segments, or the like.

The bodyside liner 25 may be any soft, flexible, porous sheet which passes fluids therethrough. The bodyside liner 25 may comprise, for example, a nonwoven web or sheet of wet strength tissue paper, a spunbonded, meltblown or bonded-carded web composed of synthetic polymer filaments, such as polypropylene, polyethylene, polyesters or the like, or a web of natural polymer filaments such as rayon or cotton. The bodyside liner 25 has a pore size that readily allows the passage therethrough of liquids, such as urine and other body exudates. The liner 25 may be selectively embossed or perforated with discrete slits or holes extending therethrough. Optionally, the web or sheet may be treated with a surfactant to aid in liquid transfer. One preferred bodyside liner material is a wettable spunbonded polypropylene having a basis weight of 0.7 ounces per square yard. Such material may be produced by the methods and apparatus described in U.S. Pat. Nos. 4,340,563 issued Jul. 20, 1982, and 4,405,297 issued Sep. 20, 1983, to Appel et al., which are incorporated herein by reference.

The absorbent core 26 is preferably an air-formed batt of cellulosic fibers (i.e., wood pulp fluff). One preferred type of wood pulp fluff, which is available under the trade designation CR1654 from Kimberly-Clark Corporation of Neenah, Wis. U.S.A., is a bleached, highly absorbent sulphate wood pulp containing softwood fibers. Optionally, the absorbent core 26 could comprise a coform material composed of a mixture of cellulosic fibers and synthetic polymer fibers. For example, the coform material may comprise an airlaid blend of cellulosic wood fibers and meltblown polyolefin fibers, such as polyethylene or polypropylene fibers.

The absorbent core 26 may also include compounds to increase its absorbency, such as an effective amount of organic or inorganic high-absorbency materials. For example, the absorbent core 26 can include 0–95 weight percent high-absorbency material. Suitable inorganic high-absorbency materials include, for example, absorbent clays and silica gels. Organic high-absorbency materials can include natural materials, such as pectin, guar gum and peat moss, as well as synthetic materials, such as synthetic hydrogel polymers. Such hydrogel polymers may include, for example, carboxymethylcellulose, alkali metal salts of polyacrylic acids, polyacrylamides, polyvinyl alcohol, ethylene maleic anhydride copolymers, polyvinyl ethers, hydroxypropyl cellulose, polyvinyl morpholinone, polymers and copolymers of vinyl sulfonic acid, polyacrylates, polyacrylamides, polyvinyl pyridine or the like. Other suitable polymers can include hydrolyzed acrylonitrile grafted starch, acrylic acid grafted starch, and isobutylene maleic anhydride copolymers, and mixtures thereof. The hydrogel polymers are preferably sufficiently cross-linked to render the materials substantially water-insoluble. Cross-linking may, for example, be by irradiation or by covalent, ionic, van der Waals, or hydrogen bonding. Suitable materials are available from various commercial vendors, such as Dow Chemical Company, Hoechst-Celanese Corporation, and Allied-Colloid. Typically, the high-absorbency material is capable of absorbing at least about 15 times its weight in water, and preferably is capable of absorbing more than about 25 times its weight in water.

The high-absorbency material can be distributed or otherwise incorporated into the absorbent core 26 employing various techniques. For example, the high-absorbency material can be substantially uniformly distributed among the fibers comprising the absorbent core. The materials can also be nonuniformly distributed within the absorbent core fibers to form a generally continuous gradient with either an increasing or decreasing concentration of high-absorbency material, as determined by observing the concentration moving inward from the backing sheet 24. Alternatively, the high-absorbency material can comprise a discrete layer separate from the fibrous material of the absorbent core 26, or can comprise a discrete layer integral with the absorbent core.

The absorbent core 26 may also include a tissue wrap layer to help maintain the integrity of the fibrous core. This tissue wrap typically comprises a hydrophilic cellulosic material, such as creped wadding or a high wet-strength tissue.

The elastic strands 38 may be formed of a dry-spun coalesced multifilament elastomeric thread sold under the trademark LYCRA and available from I.E. Du Pont de Nemours and Company. Alternately, the elastic strands 38 may be formed of other typical elastics utilized in the diaper-making art, such as a thin ribbon of natural rubber. Elasticity could also be imparted to the absorbent article by extruding a hot melt elastomeric adhesive between the backing sheet 24 and the bodyside liner 25. Other suitable elastic gathering means are disclosed in U.S. Pat. Nos. 4,938,754 issued Jul. 3, 1990, to Mesek and 4,388,075 issued Jun. 14, 1983, to Mesek et al.

The foregoing detailed description has been for the purpose of illustration. Thus, a number of modifications and changes may be made without departing from the spirit and scope of the present invention. For instance, alternative or optional features described as part of one embodiment can be used to yield another embodiment. Additionally, the components of the hook-and-loop fastening system may be reversed such that the position of hook fastening elements is switched with that of the loop fastening elements. Also, the tactile position indicators could be employed exclusively in the back waist section of a garment, which may be particularly appropriate for use by care givers to the wearer, or a single tactile position indicator could be operatively associated with each first fastening element. Likewise, the attachment system may be associated with garments other than the disposable absorbent garments as described herein. Therefore, the invention should not be limited by the specific embodiments described, but only by the claims.

We claim:

1. A method of making a disposable absorbent article, comprising the steps of:

providing a garment shell defining a first waist section, an opposite second waist section, and a crotch section between the first and second waist sections; and providing at least one first fastening element having a length dimension wherein the at least one first fastening element comprises a loop material and two second fastening elements, the second fastening elements being releasably engageable with the at least one first fastening element wherein the second fastening elements comprise a hook material;

forming a plurality of tactile position indicators, each of the tactile position indicators forming a perceptible surface irregularity having a dimension of at least about 1 millimeter and, the forming step comprising shaping the loop material to have at least one contoured side extending between opposite ends; and attaching the at least one first fastening element to the first waist section such that a plurality of discrete tactile position indicators are operatively associated with the at least one first fastening element along the length dimension.

2. A method of making a disposable absorbent article, comprising the steps of:

providing a garment shell defining a first waist section, an opposite second waist section, and a crotch section between the first and second waist sections; and providing at least one first fastening element having a length dimension and two second fastening elements, the second fastening elements being releasably engageable with the at least one first fastening element;

forming a plurality of tactile position indicators, each of the tactile position indicators forming a perceptible surface irregularity having a dimension of at least about 1 millimeter, the forming step comprising applying a room-temperature non-tacky thermally setting material to the at least one first fastening element; and attaching the at least one first fastening element to the first waist section such that a plurality of discrete tactile position indicators are operatively associated with the at least one first fastening element along the length dimension.

3. A method of making a disposable absorbent article, comprising the steps of:

providing a garment shell defining a first waist section, an opposite second waist section, and a crotch section between the first and second waist sections; and providing at least one first fastening element having a length dimension and two second fastening elements, the second fastening elements being releasably engageable with the at least one first fastening element;

forming a plurality of tactile position indicators, each of the tactile position indicators forming a perceptible surface irregularity having a dimension of at least about 1 millimeter, the forming step comprising applying a room-temperature non-tacky thermally setting material to the garment shell within about 20 millimeters of the at least one first fastening element; and attaching the at least one first fastening element to the first waist section such that a plurality of discrete tactile position indicators are operatively associated with the at least one first fastening element along the length dimension.

4. A method of making a disposable absorbent article, comprising the steps of:

providing a garment shell defining a first waist section, an opposite second waist section, and a crotch section between the first and second waist sections; and providing at least one first fastening element having a length dimension and two second fastening elements, the second fastening elements being releasably engageable with the at least one first fastening element;

forming a plurality of tactile position indicators, each of the tactile position indicators forming a perceptible surface irregularity having a dimension of at least about 1 millimeter, the forming step comprising positioning a plurality of strand segments between the at least one first fastening element and the garment shell; and attaching the at least one first fastening element to the first waist section such that a plurality of discrete tactile position indicators are operatively associated with the at least one first fastening element along the length dimension.

5. A garment, comprising:

a garment shell defining a first waist section, an opposite second waist section, and a crotch section between the first and second waist sections;

at least one first fastening element attached to or formed from the garment shell in the first waist section, the at least one first fastening element having a length dimension and a plurality of discrete tactile position indicators operatively associated with the at least one first fastening element along the length dimension, each of the tactile position indicators forming a perceptible surface irregularity having a dimension of at least about 1 millimeter, and wherein the at least one first fastening element comprises a loop material attached to the garment shell, the loop material having opposite ends and sides extending between the ends, and the contour of at least one side defines tactile position indicators; and means for releasably connecting portions of the second waist section and the at least one first fastening element, the releasably connecting means comprising at least one second fastening element releasably engageable with the at least one first fastening element.

6. A garment, comprising:

a garment shell defining a first waist section, an opposite second waist section, and a crotch section between the first and second waist sections;

at least one first fastening element attached to or formed from the garment shell in the first waist section, the at least one first fastening element having a length dimension and a plurality of discrete tactile position indicators operatively associated with the at least one first fastening element along the length dimension, each of the tactile position indicators forming a perceptible surface irregularity having a dimension of at least about 1 millimeter, and wherein the tactile position indicators comprise a room-temperature non-tacky thermally setting material; and means for releasably connecting portions of the second waist section and the at least one first fastening element, the releasably connecting means comprising at least one second fastening element releasably engageable with the at least one first fastening element.

7. The garment of claim 6, wherein the at least one first fastening element comprises a loop material having opposite ends and sides extending between the ends, and the thermally setting material is attached to the garment shell adjacent at least one of the sides of the first fastening element.

8. A garment, comprising:

a garment shell defining a first waist section, an opposite second waist section, and a crotch section between the first and second waist sections;

at least one first fastening element attached to or formed from the garment shell in the first waist section, the at least one first fastening element having a length dimension and a plurality of discrete tactile position indicators operatively associated with the at least one first fastening element along the length dimension, each of the tactile position indicators forming a perceptible surface irregularity having a dimension of at least about 1 millimeter, and wherein the at least one first fastening element comprises a plurality of ridges that define the tactile position indicators and the ridges are formed by a plurality of strand segments positioned between the at least one first fastening element and the garment shell; and means for releasably connecting portions of the second waist section and the at least one first fastening element; the releasably connecting means comprising at least one second fastening element releasably engageable with the at least one first fastening element.

9. A garment, comprising:

a garment shell defining a first waist section, an opposite second waist section, and a crotch section between the first and second waist sections;

at least one first fastening element attached to or formed from the garment shell in the first waist section, the at least one first fastening element having a length dimension and a plurality of discrete tactile position indicators operatively associated with the at least one first fastening element along the length dimension, each of the tactile position indicators forming a perceptible surface irregularity having a dimension of at least about 1 millimeter, wherein the at least one first fastening element comprises a tape landing pad attached to the first waist section and the tactile position indicators comprise a room-temperature non-tacky thermally setting material bonded to the tape landing pad; and means for releasably connecting portions of the second waist section and the at least one first fastening element, the releasably connecting means comprising at least two second fastening elements attached to the second waist section, each of the at least two second fastening elements comprising a tape member releasably engageable with the tape landing pad.

10. A disposable absorbent article, comprising:

a garment shell having opposite first and second ends with sides extending between the ends, the garment shell defining a first waist section adjacent the first end, a second waist section adjacent the second end, and a crotch section between the first and second waist sections, the garment shell comprising:

a substantially liquid permeable liner;

a substantially liquid impermeable backing sheet attached to the liner; and an absorbent core sandwiched between the liner and the backing sheet;

two loop fastening elements attached to the first waist section wherein each of the loop fastening elements has opposite ends and sides extending between the ends, one of the loop fastening elements being associated with each side of the garment shell, each of the loop fastening elements having a length dimension and a plurality of discrete tactile position indicators operatively associated with the loop fastening elements along the length dimension, each of the tactile position indicators defined by the contour of at least one of the loop fastening elements forming a perceptible surface irregularity having a dimension of at least about 1 millimeter; and two hook fastening elements releasably engageable with the loop fastening elements, each of the hook fastening elements being connected to the second waist section.

11. A disposable absorbent article, comprising:

a garment shell having opposite first and second ends with sides extending between the ends, the garment shell defining a first waist section adjacent the first end, a second waist section adjacent the second end, and a crotch section between the first and second waist sections, the garment shell comprising:

a substantially liquid permeable liner;

a substantially liquid impermeable backing sheet attached to the liner; and an absorbent core sandwiched between the liner and the backing sheet;

two loop fastening elements attached to the first waist section, one of the loop fastening elements being associated with each side of the garment shell, each of the loop fastening elements having a length dimension and a plurality of discrete tactile position indicators operatively associated with the loop fastening elements along the length dimension, each of the tactile position indicators forming a perceptible surface irregularity having a dimension of at least about 1 millimeter and wherein the tactile position indicators comprise a room-temperature non-tacky thermally setting material; and two hook fastening elements releasably engageable with the loop fastening elements, each of the hook fastening elements being connected to the second waist section.

12. A disposable absorbent article, comprising:

a garment shell having opposite first and second ends with sides extending between the ends, the garment shell defining a first waist section adjacent the first end, a second waist section adjacent the second end, and a crotch section between the first and second waist sections, the garment shell comprising:

a substantially liquid permeable liner;

a substantially liquid impermeable backing sheet attached to the liner; and an absorbent core sandwiched between the liner and the backing sheet;

at least one first fastening element attached to or formed from the backing sheet in the first waist section, the at least one first fastening element having a length dimension and a plurality of discrete tactile position indicators operatively associated with the at least one first fastening element along the length dimension, each of the tactile position indicators forming a perceptible surface irregularity having a dimension of at least about 1 millimeter, and wherein the tactile position indicators comprise a room-temperature non-tacky thermally setting material; and at least two tape members attached to the second waist section and being releasably engageable with the at least one first fastening element.

13. A garment, comprising:

a garment shell defining a first waist section, an opposite second waist section, and a crotch section between the first and second waist sections;

at least one first fastening element attached to the garment shell in the first waist section, the at least one first fastening element having opposite ends and sides extending between the ends, the contour of at least one of the sides defining a plurality of discrete tactile position indicators, each of the position indicators forming a perceptible surface irregularity having a dimension of at least about 1 millimeter and being spaced from neighboring position indicators by at least about 3 millimeters; and means for releasably connecting portions of the second waist section and the at least one first fastening element, the releasably connecting means comprising at least one second fastening element releasably engageable with the at least one first fastening element.

14. The garment of claim 13, wherein each of the position indicators extends a distance of between about 1 and about 10 millimeters from the at least one of the sides and extends a distance of between about 1 and about 10 millimeters along the at least one of the sides.

15. The garment of claim 13, wherein each of the position indicators are spaced from neighboring position indicators by between about 5 and 30 millimeters.

16. A garment, comprising:

a garment shell defining a first waist section, an opposite second waist section, and a crotch section between the first and second waist sections;

at least one first fastening element attached to or formed from the garment shell in the first waist section, the at least one first fastening element having a length dimension and a plurality of discrete tactile position indicators operatively associated with the at least one first fastening element along the length dimension, each of the tactile position indicators comprising a room-temperature non-tacky thermally setting material and forming a perceptible surface irregularity having a dimension of at least about 1 millimeter; and means for releasably connecting portions of the second waist section and the at least one first fastening element, the releasably connecting means comprising at least one second fastening element releasably engageable with the at least one first fastening element.

17. The garment of claim 16, wherein the tactile position indicators are positioned on or located within about 20 millimeters of the at least one first fastening member.

18. A garment, comprising:

a garment shell defining a first waist section, an opposite second waist section, and a crotch section between the first and second waist sections;

at least one first fastening element attached to or formed from the garment shell in the first waist section, the at least one first fastening element having a length dimension and a plurality of discrete tactile position indicators operatively associated with the at least one first fastening element along the length dimension, each of the tactile position indicators comprising a ridge that forms a perceptible surface irregularity having a dimension of at least about 1 millimeter and wherein each of the ridges is defined by a strand segments positioned between the at least one first fastening element and the garment shell; and means for releasably connecting portions of the second waist section and the at least one first fastening element, the releasably connecting means comprising at least one second fastening element releasably engageable with the at least one first fastening element.

* * * * *